United States Patent [19]
Gubelmann et al.

[11] Patent Number: 5,043,494
[45] Date of Patent: Aug. 27, 1991

[54] PREPARATION OF METHYLHYDROQUINONE

[75] Inventors: Michel Gubelmann, Lyon; Christian Allandrieu, Villeubanne, both of France

[73] Assignee: Rhone-Poulenc Chimie, Courbevoie, France

[21] Appl. No.: 421,938

[22] Filed: Oct. 16, 1989

[30] Foreign Application Priority Data

Oct. 14, 1988 [FR] France ................................. 88 14362

[51] Int. Cl.$^5$ ........................ C07C 37/55; C07C 39/10
[52] U.S. Cl. .................................. 568/766; 568/651; 568/763
[58] Field of Search ............ 568/650, 651, 652, 653, 568/763, 764, 772, 766, 780

[56] References Cited

U.S. PATENT DOCUMENTS 3,728,408  4/1973  Tobias ................................. 568/780
4,283,572  8/1981  Klicker ............................... 568/783
4,709,102 11/1987  Gupta ................................. 568/780

FOREIGN PATENT DOCUMENTS 0083010  7/1983  European Pat. Off. ............ 568/650
1249739 10/1989  Japan ................................. 568/652

Primary Examiner—Werren B. Lone
Attorney, Agent, or Firm—Burns, Doane, Swecker & Mathis

[57] ABSTRACT

Methylhydroquinone (MeHQ) or methyl ether derivative thereof is prepared by contacting paramethoxyphenol or para-dimethoxybenzene with an acid catalyst, preferably a solid acid catalyst, at a temperature ranging from 100° to 300° C.

9 Claims, No Drawings

PREPARATION OF METHYLHYDROQUINONE

BACKGROUND OF THE INVENTION

1. Field of the Invention

The present invention relates to the preparation of methylhydroquinone.

2. Description of the Prior Art

Methylhydroquinone is a known compound that is a very useful intermediate in a wide variety of organic syntheses.

SUMMARY OF THE INVENTION

Briefly, the present invention features the preparation of methylhydroquinone (MeHQ) by contacting paramethoxyphenol or para-dimethoxybenzene with an acid catalyst, notably a solid acid catalyst, at a temperature ranging from 100° to 300° C.

DETAILED DESCRIPTION OF THE PREFERRED EMBODIMENTS OF THE INVENTION

More particularly according to the present invention, while a liquid acid such as sulfuric acid is a useful such acid catalyst, it is preferred to use a solid catalyst comprising acid functions within the definitions of Lewis or Bronsted acid. Such solid catalysts are defined as any solids having a cation-exchange capacity which has been partially or completely exchanged by $H^+$ and/or a Lewis acid ($M^{n+}$ where $n>3$). Exemplary of these solids, the following are particularly representative:

(a) clays that have been treated with a strong acid;
(b) zeolites that have also been exchanged;
(c) crosslinked sulfonated resins of the styrene/divinylbenzene type and Nafion ® (a perfluorinated and sulfonated resin marketed by Dupont de Nemours);
(d) acid or amphoteric oxides, the reactivity of which has been increased by treatment with an acid; and
(e) heteropolyacids, such as the phosphomolybdic acids and the phosphotungstic acids.

The reaction temperatures according to the invention can vary widely over the broad range of from about 100° to about 300° C. Best results are obtained using a temperature ranging from 150° to 250° C.

The reaction can thus be represented:

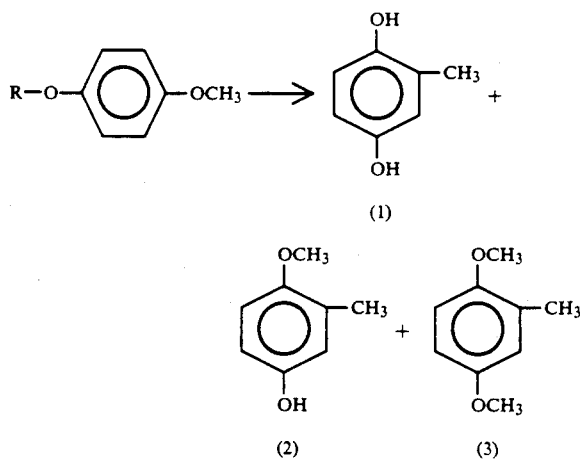

wherein R is $CH_3$ or H.

The compound (1) is methylhydroquinone, the desired final product, and compounds (2) and (3) are methylated derivatives (of the OH radical or radicals) of methylhydroquinone. The compounds (2) and (3) are readily converted into methylhydroquinone, and thus are useful "precursors" of methylhydroquinone.

When para-methoxyphenol is used as the starting material, methylhydroquinone will be produced in a high yield and with relatively few of the "precursors" described above.

When para-dimethoxybenzene is used as the starting material, larger proportions of such "precursors" will be produced. However, it will be appreciated that paradimethoxybenzene is a particularly attractive starting material because it is a by-product from the polyphenol chemical industry. Thus, its value is enhanced.

While the subject reaction mechanism appears to be relatively simple when para-methoxyphenol is used as the starting material (while not wishing to be bound to any particular theory, it is probably a dealkylation reaction followed by an alkylation reaction on an adjacent carbon atom of the ring, or an intramolecular reaction), the mechanism becomes very complex, and is still largely hypothetical and therefore unknown, when para-dimethoxybenzene is used as the starting material.

In order to further illustrate the present invention and the advantages thereof, the following specific examples are given, it being understood that same are intended only as illustrative and in nowise limitative.

EXAMPLE 1

(liquid phase)

5.7 g (46 mmoles) of para-methoxyphenol and 1 g of ultrastabilized commercial zeolite of the faujasite type (US-Y marketed by Toyo-Soda) were introduced into a 50 cm³ glass tube. The tube was sealed and inserted into a metallic sheath. The assembly was placed in a balancing furnace known as a "Carius" furnace and heated to 200° C. for 2.5 hours.

The solid catalyst was recovered by filtration on fritted glass and washed with ethyl acetate. The solution was analyzed by gas phase chromatography, and the nature of the final products was confirmed by a complete spectroscopic analysis (infrared, nuclear magnetic resonance, mass spectrometry).

The results obtained evidenced that:

(i) the degree of conversion of the paramethoxyphenol was 54%;
(ii) the yield of methylhydroquinone and "precursors" from the reaction was 11%.

EXAMPLE 2

(liquid phase)

The procedure of Example 1 was repeated, but using para-dimethoxybenzene as the starting material.

The degree of conversion was 57% and the yield 52%.

EXAMPLE 3

(liquid phase)

The procedure of Example 2 was repeated, but using a commercial acid clay (KSF montmorillonite marketed by SudChemie) in place of the zeolite.

The degree of conversion was 58% and the yield 45%.

EXAMPLE 4

(vapor phase)

1 g of an ultrastabilized commercial zeolite of the faujasite type (US-Y marketed by Toyo-Soda) and 6 g of quartz particles, 1 mm in diameter, were introduced into a quartz tube. This catalytic bed was heated to 400° C. for 10 hours. The bed was then cooled to 200° C.

A current of nitrogen and para-dimethoxybenzene was introduced into a tube, and a gaseous flowstream comprising 1 l per hour nitrogen and 9 mmoles per hour paradimethoxybenzene was passed over the catalytic bed. The contact time was 2 3 seconds.

At the outlet of the reactor, the reaction products were trapped and then analyzed The mean degree of conversion (during the duration of the experiment, which was 3 hours) was 23% and the yield 31%.

EXAMPLE 5

(vapor phase)

The procedure of Example 4 was repeated, but employing a reaction temperature of 240° C.

The mean degree of conversion (duration of the experiment, 1.8 hours) was 12% and the yield 22%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of methylhydroquinone or methyl ether derivative thereof, comprising contacting para-methoxyphenol or paradimethoxybenzene with a solid acid catalyst at an elevated temperature ranging from about 100° to 300° C.

2. The process as defined by claim 1, said solid catalyst comprising a Lewis or Bronsted acid.

3. The process as defined by claim 2, said solid catalyst comprising a strong acid-treated clay.

4. The process as defined by claim 2, said solid catalyst comprising an ion-exchanged zeolite.

5. The process as defined by claim 2, said solid catalyst comprising a styrene/divinylbenzene sulfonated resin.

6. The process as defined by claim 2, said solid catalyst comprising an acid-treated, acid or amphoteric oxide.

7. The process as defined by claim 2, said solid catalyst comprising a heteropolyacid.

8. The process as defined by claim 1, carried out in liquid phase.

9. The process as defined by claim 1, carried out in vapor phase.

* * * * *